US00PP13200P2

(12) United States Plant Patent
Griesbach et al.

(10) Patent No.: US PP13,200 P2
(45) Date of Patent: Nov. 12, 2002

(54) ORNITHOGALUM PLANT NAMED 'CHESAPEAKE SNOWFLAKE'

(75) Inventors: Robert Griesbach, Ellicott City, MD (US); Fred Meyer, deceased, late of Escondido, CA (US), by Marlene Estella Meyer, legal representative

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 74 days.

(21) Appl. No.: 09/853,292

(22) Filed: May 11, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ornithogalum plant named 'Chesapeake Snowflake' characterized by its strong, upright and short scapes; and dense corymbose racemes with numerous white-colored flowers.

1 Drawing Sheet

BACKGROUND OF THE INVENTION

The present Invention relates to a new and distinct cultivar of Ornithogalum plant, botanically known as *Ornithogalum thyrsoides*, and hereinafter referred to by the name 'Chesapeake Snowflake'.

The new Ornithogalum is a product of a planned breeding program conducted by the Inventors in Beltsville, Md. The objective of the breeding program was to create new freely-flowering Ornithogalums with desirable flower colors and strong short scapes.

The new Ornithogalum originated from a cross made by the Inventors of the *Ornithogalum thyrsoides* cultivar Bok Bay, not patented, as the female or seed parent with an unidentified selection of *Ornithogalum thyrsoides*, not patented, as the male or pollen parent. The cultivar Chesapeake Snowflake was discovered and selected by the Inventors as a flowering plant within the progeny of the stated cross in a controlled environment in Beltsville, Md. in 1994.

Asexual reproduction of the new Ornithogalum by tissue culture in a controlled environment in a laboratory in Beltsville, Md., has shown that the unique features of this new Ornithogalum are stable and reproduced true to type in successive generations.

SUMMARY OF THE INVENTION

The cultivar 'Chesapeake Snowflake' has not been observed under all possible environmental conditions. The phenotype may vary somewhat with variations in environment such as temperature, daylength, light intensity, and water or nutritional status without, however, any variance in genotype.

The following traits have been repeatedly observed and are determined to be the unique characteristics of 'Chesapeake Snowflake'. These characteristics in combination distinquish 'Chesapeake Snowflake' as a new and distinct Ornithogalum:

1. Strong, upright and short scapes.

2. Dense corymbose racemes with numerous white-colored flowers.

In side-by-side comparisons conducted by the Inventors in Beltsville, Md., plants of the new Ornithogalum differ from plants of the female parent, the cultivar Bok Bay, in the following characteristics:

1. Plants of the new Ornithogalum flower about five weeks earlier than plants of the cultivar Bok Bay.

2. Plants of the new Ornithogalum have shorter inflorescences and shorter scapes than plants of the cultivar Bok Bay.

3. Plants of the new Ornithogalum have white-colored flowers whereas plants of the cultivar Bok Bay have cream-colored flowers.

In side-by-side comparisons conducted by the Inventors in Beltsville, Md., plants of the new Ornithogalum differ from plants of male parent, the unidentified selection of *Ornithogalum thyrsoides*, in the following characteristics:

1. Plants of the new Ornithogalum are more freely flowering than plants of the unidentified selection of *Ornithogalum thyrsoides.*

2. Plants of the new Ornithogalum have stronger scapes than plants of the unidentified selection of *Ornithogalum thyrsoides.*

3. Plants of the new Ornithogalum have a denser (less open) flower display than plants of the unidentified selection of *Ornithogalum thyrsoides.*

BREIF DESCRIPTION OF THE PHOTOGRAPH

The accompanying colored photograph illustrates the overall appearance of the new Ornithogalum, showing the colors as true as it is reasonably possible to obtain in colored reproductions of this type. Colors in the photograph may differ slightly from the color values cited in the detailed botanical description which accurately describe the colors of the new Ornithogalum.

The photograph comprises a side perspective view of a typical flowering plant of 'Chesapeake Snowflake'.

DETAILED BOTANICAL DESCRIPTION

In the following description, color references are made to The Royal Horticultural Society Colour Chart except where general terms of ordinary dictionary significance are used. The following observations and measurements describe plants grown in Beltsville, Md., under commercial practice in a glass-covered greenhouse. During the production of the plants, day temperatures ranged from 20 to 32° C. and night temperatures ranged from 14 to 26° C. Measurements and numerical values represent averages for typical flowering plants. Plants used for the description and photograph were grown in 12.5-cm containers for about 20 to 25 weeks after planting rooted tissue-cultured plantlets in the fall.

Botanical classification: *Ornithogalum thyrsoides* cultivar Chesapeake Snowflake.

Parentage:

*Female or seed parent.*—*Ornithogalum thyrsoides* cultivar Bok Bay, not patented.

*Male or pollen parent.*—Unidentified selection of *Ornithogalum thyrsoides*, not patented.

Propagation:

*Type.*—Tissue culture.

*Time to initiate roots from tissue-cultured micro-cuttings.*—About 10 days at 24° C.

*Root description.*—Quantity: About 30 to 40 primary roots arising from bulb. Root ball diameter: About 12 to 13 cm. Color: 159C.

*Bulb description.*—Appearance: Tunicate. Diameter: About 3.5 cm. Circumference: About 11 to 11.5 cm. Color: 161B.

Plant description:

*Plant form.*—Upright flowering potted plant; inverted triangle. Leaves basal with central flowering stem. Flowers arranged in dense corymbose racemes.

*Crop time.*—Usually about 20 to 25 weeks are required to produce finished flowering plants in 12.5-cm containers from rooted tissue-culture plantlets.

*Plant height.*—About 20 to 30 cm.

*Plant width.*—About 30 to 40 cm.

*Leaves.*—Arrangement: Simple; basal; rosette; sessile. Quantity of leaves per plant: At least 6 to 8. Length: About 25 to 30 cm. Width: About 3.5 to 4 cm. Shape: Lanceolate. Apex: Acute. Margin: Entire. Texture: Glabrous, smooth; longitudinally ridged. Venation pattern: Parallel. Color: Young and mature leaves, upper and lower surfaces: 143B; upper surface, slightly glossy; venation, both surfaces, 143B. Leaf sheath: Length: About 3.5 to 4 cm. Width: About 5.5 to 6 cm. Color: 155B.

Flower description:

*Flowering habit.*—Inflorescences scapose with single flowers, 3-merous, arranged in dense corymbose racemes. Flowers not fragrant; flowers persistent.

*Natural flowering season.*—Plants flower during the spring; flowering recurrent.

*Flower longevity on the plant.*—Individual flowers last about one week; inflorescences last about six weeks.

*Flower longevity as a cut flower.*—Inflorescences last about 5 to 6 weeks.

*Inflorescence size.*—Length: About 25 cm. Width: About 10 cm.

*Flower buds.*—Length: About 1.2 to 1.5 cm. Diameter: About 8 to 10 mm. Shape: Ovoid. Color: 145B.

*Flowers.*—Quantity of flowers and flower buds per plant: About 40 to 50 per flowering stem; each bulb produces about three to four flowering stems at a time. Shape: Circular. Diameter: About 5 to 6 cm. Depth (height): About 2 cm.

*Perianth.*—Quantity/arrangement: Three petals and three sepals per flower; separate. Length: About 2 to 2.5 cm. Width: About 1.5 cm. Shape: Pyriform. Apex: Rounded to acute. Margin: Entire. Texture: Smooth, waxy. Color: When opening, upper and lower surfaces: 155A. Fully opened, upper and lower surfaces: 155D with 147A spot at base; glossy.

*Scape.*—Angle: Erect. Strength: Strong. Length: About 20 cm. Diameter: About 1 cm. Texture: Glabrous. Color: 137A.

*Pedicels.*—Strength: Strong. Length: About 4.5 to 5 cm. Diameter: About 3 mm. Texture: Glabrous. Color: 144B.

*Flower bracts.*—Arrangement: Single, subtending the perianth. Length: About 4 to 4.5 cm. Width: About 1.2 to 1.5 cm. Shape: Cymbiformis. Color: 137A.

*Reproductive organs.*—Stamens: Quantity: Six. Anther shape: Oval. Anther length: About 2 to 3 mm. Anther color: 163B. Amount of pollen: Moderate. Pollen color: 163B. Pistils: Quantity: One. Length: About 8 to 10 mm. Stigma shape: Tri-sulcate. Stigma color: 158A. Style length: About 2 mm. Style color: 158A. Ovary color: 146B.

*Seed.*—Seed production has not been observed.

Disease resistance: Resistance to pathogens common to Ornithogalums has not been determined.

It is claimed:

1. A new and distinct cultivar of Ornithogalum plant named 'Chesapeake Snowflake', as illustrated and described.

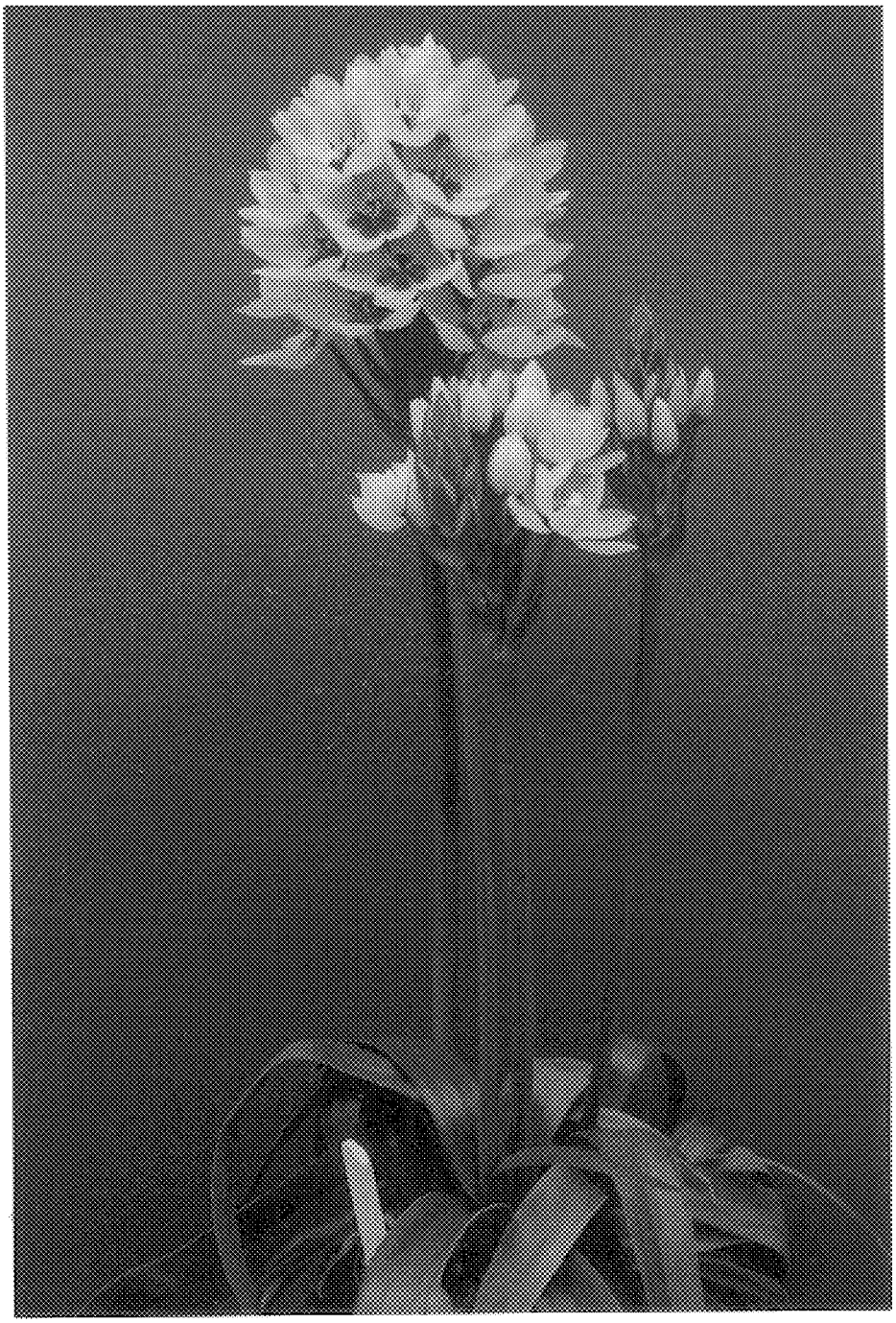

* * * * *